United States Patent [19]

Lang et al.

[11] Patent Number: 5,492,650
[45] Date of Patent: Feb. 20, 1996

[54] MICROBICIDAL AGENT CONTAINING POLYMERIC QUATERNARY AMMONIUM BORATE FOR PRESERVING AND DISINFECTING INDUSTRIAL PRODUCTS AND INDUSTRIAL PLANTS

[75] Inventors: Frank Lang, Hatterscheim am Main; Erich Gatter, Kastl; Helmut Berenbold, Wiesbaden; Detlef Wehle, Niedernhausen, all of Germany

[73] Assignee: Hoechst Aktiengesellschaft, Frankfurt am Main, Germany

[21] Appl. No.: 992,582

[22] Filed: Dec. 18, 1992

[30] Foreign Application Priority Data

Dec. 20, 1991 [DE] Germany .................. 41 42 424.7

[51] Int. Cl.$^6$ .................................. C14C 9/00
[52] U.S. Cl. .............. 252/380; 252/8.57; 252/400.41; 422/1; 422/28; 422/32; 424/404; 424/405; 514/64; 514/642
[58] Field of Search ............ 210/764; 252/106, 252/857, 380, 400.41, 106, 49.6; 424/404, 405; 8/490, 188, 94.1 R; 422/1, 28, 32; 514/642, 64, 642

[56] References Cited

U.S. PATENT DOCUMENTS

| | | | |
|---|---|---|---|
| 3,140,976 | 7/1964 | Berenschot | 210/764 |
| 3,596,870 | 8/1971 | Walker | 249/156 |
| 3,764,593 | 10/1973 | Schuster . | |
| 4,166,725 | 9/1979 | Amick . | |
| 4,257,769 | 3/1981 | Kleber et al. | 8/188 |
| 4,778,813 | 10/1988 | Fenyes et al. | 8/188 |
| 4,824,484 | 4/1989 | Metzner et al. | 106/18.31 |
| 4,970,201 | 11/1990 | Giebeler et al. . | |
| 4,976,874 | 12/1990 | Gannon et al. | 210/764 |
| 4,994,199 | 2/1991 | Scardera et al. | 514/642 |
| 5,087,457 | 2/1992 | Bryant et al. | 514/642 |
| 5,192,451 | 3/1993 | Gill | 210/764 |

FOREIGN PATENT DOCUMENTS

| | | |
|---|---|---|
| 0049017 | 4/1982 | European Pat. Off. . |
| 0498162 | 8/1992 | European Pat. Off. . |
| 4118895 | 3/1992 | Germany . |

*Primary Examiner*—Philip Tucker
*Assistant Examiner*—Valerie Fee
*Attorney, Agent, or Firm*—Connolly & Hutz

[57] ABSTRACT

The invention relates to the use of a microbicidal agent containing polymeric quaternary ammonium borate, obtained by simultaneous reaction of amines of the formula I or II

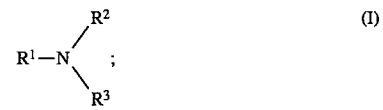

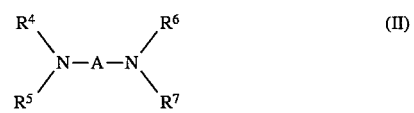

in which $R^1$ to $R^7$ and A are as defined in the description, with 1 to 20 mol of ethylene oxide or propylene oxide and 0.6 to 1.5 mol of boric acid, boric acid esters or salts of boric acid, in each case per mole of nitrogen equivalent, as a preservative and/or disinfectant for industrial products and industrial plants.

6 Claims, No Drawings

MICROBICIDAL AGENT CONTAINING POLYMERIC QUATERNARY AMMONIUM BORATE FOR PRESERVING AND DISINFECTING INDUSTRIAL PRODUCTS AND INDUSTRIAL PLANTS

It is known that quaternary ammonium compounds, such as alkylbenzyldimethylammoniumchloride, are compounds which have a good microbicidal action. This term microbicidal action is understood as meaning bactericidal, fungicidal and algicidal activity in the customary sense.

It is also known that quaternary ammonium compounds, on their own or in combination with other microbicidal active substances such as alcohols or aldehydes, are used for disinfection or for preservation (see K. H. Wallhäuser, "Sterlisation—Desinfektion—Konservierung" [Sterilization—Disinfection—Preservation], Georg Thieme Verlag Stuttgart, 3rd Edition, 1984, pages 133, 472).

EP-A-0 355 316 discloses the use of quaternary ammonium borates as agents for preserving wood, wood materials and other cellulose-containing products.

However, the quaternary ammonium compounds which are known to date have a series of disadvantages. For example, it has emerged that in particular quaternary ammonium halides have a corrosive effect on metals. This means that there is only a limited use for quaternary ammonium compounds in industrial disinfection, such as disinfection of instruments. Moreover, quaternary ammonium compounds foam greatly, both in water-containing and in solvent-containing mixtures. This behavior is of considerable disadvantage for use in machines and apparatus in which the compounds are subjected to intensive mechanical treatment.

This means that there was a continued demand for the provision of quaternary ammonium compounds which have good microbicidal properties, which are weakly corrosive and whose tendency to foam is only slight and which are suitable as preservatives and/or disinfectants for industrial products and industrial plants.

Surprisingly, it has emerged that solutions or microemulsions of polymeric quaternary ammonium borates in water or in organic solvents are suitable as microbicidal agents which are only weakly corrosive and only have a slight tendency to foam and which are used as disinfectants and/or preservatives for industrial products and industrial plants due to these properties.

The invention relates to the use of a microbicidal agent containing polymeric quaternary ammoniumborate, obtained by simultaneous reaction of amines of the formula I or II $$R^1-N\begin{array}{c}R^2\\ \\R^3\end{array} \quad (I)$$

$$\begin{array}{c}R^4\\ \\R^5\end{array}N-A-N\begin{array}{c}R^6\\ \\R^7\end{array} \quad (II)$$

having 1 to 20, preferably 3 to 10, mol of ethylene oxide or propylene oxide and 0.6 to 1.5, preferably 1, mol of boric acid, boric acid esters or salts of boric acid, in each case per mole of nitrogen equivalent, in which $R^1$ is $C_8$–$C_{22}$-alkyl or $C_8$–$C_{22}$-alkenyl or, if $R^2$ and $R^3$ are groups of the formula —$(C_2H_4O)_xH$ or —$(C_3H_6O)_xH$, $R^1$ can also be $C_1$–$C_4$-alkyl, $R^2$ is hydrogen, $C_1$–$C_{22}$-alkyl or a group of the formula —$C_1$–$C_{22}$-alkyl or a group of the formula —$(C_2H_4O)_xH$, —$(C_3H_6O)_xH$ or —$CH_2CH_2CH_2NH_2$, $R^3$ is hydrogen or a group of the formula —$(C_2H_4O)_xH$, —$(C_3H_6O)_xH$ or —$CH_2CH_2CH_2NH_2$, $R^4$ and $R^6$ are $C_1$–$C_4$-alkyl or a group of the formula —$(C_2H_4O)_xH$ or —$(C_3H_6O)_xH$, $R^5$ and $R^7$ are a group of the formula —$(C_2H_4O)_xH$ or —$(C_3H_6O)_xH$, A is a group of the formula —$(CH_2)_n$—, —$(CH_2CH_2OCH_2CH_2)_n$— or —$(CH_2CH_2NHCH_2CH_2)_n$—, x represents numbers from 1 to 55 and n is an integer from 1 to 20, as preservatives and/or disinfectants for industrial products and industrial plants.

The following are preferred amines of the above formulae:

1. Amines of the formula I in which $R^1$ is $C_8$–$C_{22}$-alkyl, $R^2$ is $C_8$–$C_{22}$-alkyl or $C_1$–$C_4$-alkyl and $R^3$ is hydrogen or a group of the formula —$(C_2H_4O)_xH$ or —$(C_3H_6O)_xH$.

2. Amines of the formula I in which $R^1$ is $C_8$–$C_{22}$-alkyl and $R^2$ and $R^3$ are hydrogen.

3. Amines of the formula I in which $R^1$ is $C_8$–$C_{22}$-alkyl or $C_8$–$C_{22}$-alkyl and $R^2$ and $R^3$ are groups of the formula —$(C_2H_4O)_xH$ or —$(C_3H_8O)_xH$ in which the total of the ethylene oxide groups in the two radicals $R^2$ and $R^3$ is 2 to 20.

4. Amines of the formula I in which $R^1$ is $C_8$–$C_{22}$-alkyl, $R^2$ is hydrogen or a group of the formula —$CH_2CH_2CH_2NH_2$ and $R^3$ is a group of the formula —$CH_2CH_2CH_2NH_2$.

5. Amines of the formula II in which A, $R^4$, $R^5$, $R^6$ and $R^7$ are as defined above and in which the total of all ethylene oxide groups is 4 to 30.

From the alkylene oxide groups of the formulae —$(C_2H_4O)_xH$ and —$C_3H_6O)_xH$, the group of the formula —$(C_2H_4O)_xH$ is preferred. Instead of the pure polyoxyethylene and polyoxypropylene groups, radicals can also be constructed of both ethylene oxide and propylene oxide units.

The amines are reacted with boric acid and the alkylene oxide in such a manner that the particular amine and boric acid are introduced into an autoclave, and the alkylene oxide is metered in. In general, the reaction temperature is 60° to 130° C., preferably 60° to 125° C., in particular 60° to 100° C. The reaction pressure is 50 to 600 kPa. Under these reaction conditions, the alkylene oxide is metered in over a period from 1 to 5 hours. The mixture is kept for 3 to 12 hours at a temperature of 70° to 120° C., preferably 70° to 100° C., under the pressure indicated, in order for the reaction to continue.

Instead of boric acid, its esters such as, for example, trimethylboric acid ester, or its salts, for example sodium borate, can also be employed. Water and polyglycols are formed in the reaction as secondary products. The resulting polymeric quaternary ammonium compounds contain as structural characteristic essentially groups of the formula $$-\overset{R^1}{\underset{R^2}{\overset{|}{{}^+N}}}-(CH_2CH_2O)_x-\overset{O^-}{\underset{}{\overset{|}{B}}}-(OCH_2CH_2)_y-$$

or groups of the formula $$-\overset{R^4}{\underset{R^5}{\overset{|}{{}^\pm N}}}-A-\overset{R^6}{\underset{R^7}{\overset{|}{{}^\pm N}}}(\!\!-CH_2CH_2O\!\!)_x\overset{O^-}{\underset{}{\overset{|}{B}}}(\!\!-OCH_2CH_2\!\!)_y O-\overset{O^-}{\underset{}{\overset{|}{B}}}(\!\!-OCH_2CH_2\!\!)_z$$

if the reaction has been carried out with ethylene oxide. The presence of polymeric or oligomeric quaternary ammonium borates can already been seen from the fact that water is formed in the reaction between amines of the formulae I and II with boric acid and alkylene oxide, as shown by the examples.

These crude solutions contain generally approximately 6–12% of water and approximately 8–12% of glycols, due to their preparation. These secondary products, in particular the glycols, can be removed; however, this is unnecessary for their use in practice.

When the reaction has ended, the resulting crude solution of the polymeric quaternary ammonium borates can be used for the abovementioned purpose directly as a concentrate without further purification and working-up, or else it can be processed with other microbicidal active substances and, if appropriate, with additives known per se to give the microbicidal agent according to the invention, which may have a widened spectrum of action. Additional microbicidal active substances can be quaternary ammonium salts such as alkylbenzyldimethylammonium salts or dialkyldimethylammonium salts, fatty amines, amines, lower alcohols such as ethanol, propanol, aldehydes such as formaldehyde, glutardialdehyde and glyoxal, guanidines such as alkylguanidines and alkyldiguanidines and phenol derivatives such as salicylates, all of which can be used in aqueous as well as in substantially anhydrous preparations. Examples of other additives are perfume or colorants.

The microbicidal agents in the form of their concentrates contain 0.1–70% by weight, preferably 5–40% by weight, of the abovementioned polymeric quaternary ammonium borates, 99.9–30% by weight, preferably 95–60% by weight, of other biocidal active substances and, if appropriate, 0–50% by weight of additives.

The novel and the known microbicidal agents in the form of their concentrates can be diluted with water or non-aqueous solvents. They can be mixed with water at any desired ratio, resulting in stable solutions or microemulsions. The concentrates also have good miscibility with non-aqueous solvents. The substantially anhydrous preparations of the crude solutions are obtained by dissolving the concentrates in a solvent or, preferably, in a solvent mixture. Suitable non-aqueous solvents are glycols, glycol ethers, ethers, lower alcohols or mixtures of these solvents with chloroform or methylene chloride. An addition of 5–25% by weight of polyhydric alcohols, in particular polypropylene glycol, results in clear solutions as essentially aqueous preparations. The preferred solvent mixture consists of a higher-boiling polyol component, such as polyethylene glycol or di- or tripropylene glycol methyl ester and an amount of one or more lower-boiling solvents such as ®Shellsol AB (manufacturer: Shell AG), n-hexane, toluene, cyclohexane, chloroalkanes, ketones or lower alcohols.

The novel and the known microbicidal agents can contain 1–99% by weight of the abovementioned solvents, as an individual component or in the form of a mixture. The viscosity of the concentrates and solutions, or microemulsions, is between 1 and 100 Pas, but can reach up to 300 Pas in individual cases. The viscosity of the polymeric quaternary ammonium borates depends on the reaction temperature, higher reaction temperatures result in lower viscosities.

The novel and the known microbicidal agents can be employed for the preservation and/or disinfection of industrial products and industrial plants. Preservation is to be understood mainly as protection against microbial attack and destruction caused by bacteria, fungi, algae and the like. Disinfection is to be understood as meaning the destruction, or inactivation, of bacteria, viruses, fungi, algae and the like on, or in, industrial plants, objects and on the hands and the skin. Industrial plants are to be understood, for example, as meaning water circuits, water containers, heat exchangers and oil-drilling and oil-recovery gear, in particular in the secondary recovery of mineral oil. Industrial products are to be understood as meaning, for example, polymer dispersions, glues, jointing compounds, colors, coatings, textiles, leather, disinfecting detergents and cooling lubricants.

The novel and the known microbicidal agents are also suitable as disinfectants, in particular for the disinfection of surfaces and instruments, and as cleaning disinfectants as they are used mainly for cleaning buildings and domestic cleaning.

For the preservation of leather, the material to be preserved, preferably chrome-tanned leather (wet blue), is treated in a suitable apparatus, preferably in a barrel, at 20 to 200% by weight of liquor, based on the weight of leather, and conventionally at a temperature from 15° to 45° C. over a period of 10 minutes to 12 hours, preferably 30 minutes to 2 hours. The amount of polymeric quaternary ammoniumborate (active substance) employed is conventionally in the range between 0.1 and 10% by weight, preferably 0.5 to 2% by weight, based on the weight of leather. Besides the microbicidal agent, the aqueous liquor contains the compounds conventionally employed in chrome tanning.

To preserve the hide, the material to be preserved, preferably a soaked hide from which, if appropriate, the flesh may have been removed, is treated in a suitable apparatus, preferably in a barrel, at 20 to 200% by weight of liquor based on the weight of hide and conventionally at a temperature from 15° to 35° C. over a period from 10 minutes to 5 hours, preferably 30 minutes to 3 hours. The amount of polymeric quaternary ammonium borate (active substance) employed is conventionally in the range between 0.4 and 10% by weight, preferably 1 to 5% by weight, based on the weight of hide. The aqueous liquor has the composition usually employed for the preservation of hide and additionally contains the microbicidal agent.

For the purposes of preservation and/or disinfection, the microbicidal agents in the form of the concentrates or dilutions are applied to the industrial product or plant in question. Application is effected by conventional, known processes such as spraying, brushing on or pouring.

It is also feasible to immerse the object in question in the microbicidal agent.

The above-described polymeric quaternary ammonium borates can also act as microbicidal additives in the formulation of disinfecting detergents in combination with customary anionic, non-ionic, cationic and amphoteric surfactants. Anionic surfactants which are suitable for this purpose are, for example, soap, fatty alcohol sulfates, alkyl ether sulfates, fatty acid condensation products such as taurides, methyltaurides, sarcosides, furthermore α-olefinsulfonates, hydroxyalkanesulfonates, secondary alkanesulfonates, amide ether sulfates or alkylbenzene-sulfonates. Non-ionic surfactants which can be used are, for example, polyglycol monoalkyl ethers and polyglycol monoesters, amine oxides and ethylene oxide/propylene oxide condensation products. A combination with other amphoteric surfactants such as alkylbetaines, alkylaminobetaines, imidazoline derivatives or sulfobetaines is furthermore possible. Finally, the agents can also be employed in the form of a mixture with fatty amines, with cationic surfactants such as ammonium and phosphonium salts, quaternized ether amines or polymeric quaternary ammonium compounds. Non-ionic surfactants are preferred. If appropriate, they may contain further additives which are used in the customary manner in detergents.

These are, for example, viscosity-increasing or -reducing compounds such as cellulose ethers, electrolytes such as, for example, sodium chloride or ammonium chloride, fatty acid polyglycol esters, alkanolamides, magnesium aluminum silicates, polyglycol, glycerol and ethanol. When the active substances are processed to give pulverulent preparations, it is furthermore possible to use conventionally used fillers and carriers such as highly-disperse amorphous silica, sodium sulfate, magnesium aluminum silicate, starch derivatives and the like. Other customary additives are bleaching agents, chlorine-eliminating substances, chelating agents and, if appropriate, also polymer dispersions.

Examples for the preparation of the polymeric quaternary ammonium borates are described in EP-A-0 355 316 (page 4 to page 8).

Preparation example (corresponds to Example 13 of EP-A-0 355 316):

Unless otherwise indicated, the percentages are percent by weight. The viscosity is determined using a ®Haake RV 12 (manufacturer: Haake, Germany) at a temperature of 25° C. and a velocity gradient of $D=21$ $s^{-1}$. The water content is determined by the method of Karl Fischer.

so that the end concentrations of the active substance given in Table 1 resulted. 2.0 ml of sterile distilled water were added to a control tube.

With regard to the preparation of the inoculum, the procedure was as in the NCCLS/FDA recommendations. Following cultivation on solid media, purity checks and identity checks, sterile Müller-Hinton broth was inoculated with a few colonies and incubated until visible clouding was observed. These cultures were diluted by an addition of sterile broth in such a way that they corresponded to a cloudiness of 0.5 of the McFarland standard (=approx. 10(8) colony-forming units (CFU)/ml). After a further 1:100 dilution, 1.0 ml aliquots of the microorganism suspension were pipetted into all tubes (density: approx. 5×10(5) CFU/ml of broth).

The tubes were incubated for 20 hours (yeasts and molds 48 hours) at 36°±1° C. and then tested for microbial growth (cloudiness). Subcultures in the border range and from the control tubes were grown on suitable solid media as a purity and identity check. Growth was recorded as +, no growth as −.

The complete experiment was replicated in an independent experiment. The results were reproduced in all cases.

The concentration of active substance at which no growth of microorganisms was detectable was indicated as MIC.

TABLE 1

Results of the broth dilution test

| Test microorganism | Concentration of active substance in µg/ml | | | | | | | | | MIC in µg/ml |
|---|---|---|---|---|---|---|---|---|---|---|
| | 512 | 256 | 128 | 64 | 32 | 16 | 8 | 4 | K | |
| Pseudomonas aeruginosa | − | − | − | + | + | + | + | + | + | 128 |
| Proteus mirabilis | − | − | − | − | + | + | + | + | + | 64 |
| Staphylococcus aureus | − | − | − | − | − | − | + | + | + | 16 |
| Candida albicans | − | − | − | − | − | + | + | + | + | 32 |
| Aspergillus niger | − | − | − | − | − | − | − | + | + | 8 |

A mixture of 206.5 g (0.70 mol) of didecylamine (amine number 190.2) and 43.3 g (0.70 mol) of boric acid in 42.4 g of water was introduced into a 1 l glass autoclave, the mixture was heated at a temperature of 78° C., and 138.2 ml (123.3 g, 2.80 mol) of liquid ethylene oxide was subsequently metered in in the course of 2.5 hours at a temperature of 78°–88° C. and a pressure of 80–340 kPa. When the addition had ended, the reaction was allowed to continue for 7 hours at 80° C., and was then stopped. The pale yellow, viscous, homogeneous reaction mixture was characterized by the following analytical data: viscosity: 3.8 Pa.s, water: 18%, ethylene glycol: 5.4%, diethylene glycol: 2.3%, triethylene glycol: 1.4%, pH 10.0. An ethylene oxide balance was used for calculating a statistic value of 3.1 mol of chemically bonded ethylene oxide per nitrogen equivalent.

The polymeric quaternary ammoniumborate prepared by this example was used in the following use examples.

Use examples:

Determination of the microbicidal action:

The microbicidal action of polymeric quaternary ammonium borate was determined via the minimum inhibitory concentration (MIC) in the broth dilution test according to DIN 58940 (Part 5 and Supplement 1 dated June 1989).

Procedure:

1.0 g of sample, weighed accurately, was prediluted with sterile distilled water. 2.0 ml aliquots of the dilute sample were pipetted into tubes containing 20 ml of double-concentrated Müller-Hinton broth (Merck, Article No. 10293)

Determination of the corrosion-inhibiting action:

To determine the corrosion-inhibiting action, steel coupons were half-immersed in solutions of the polymeric quaternary ammonium borate at various concentrations. The steel coupons were stored in the solution over a period of 7 days at a temperature of 25° C., and the amount of metal removed was subsequently determined. To this end, corroded parts of the steel coupon were removed and the weight loss was determined. The percentage weight loss is termed amount of metal removed.

TABLE 2

Results of the corrosion-inhibiting action

| Active substance concentration [% by weight] | Amount of metal removed [% by weight] |
|---|---|
| 0.1 | <0.02%[+)] |
| 0.5 | <0.02%[+)] |
| 1.0 | <0.02%[+)] |
| 2.5 | <0.02%[+)] |
| 5.0 | <0.02%[+)] |

[+)]The values for the amount of metal removed from the steel coupons are within the range of error.

The corrosion of the steel coupons in fully demineralized water was determined for comparison purposes. The amount of metal removed was 0.23% by weight.

7

Determination of the foaming behavior:

The foaming behavior of the polymeric quaternary ammonium borate was determined according to DIN 53902 (Part 1 dated March 1981, "Götte beaten foam"). To this end, solutions with various active substance contents were prepared at a temperature of 25° C. The foam was produced by beating the solution in a measuring cylinder thirty times using a perforated plate attached to a rod. The foam volume of the sample solution was determined 30 seconds after beating had ended by reading off the foam volume in the measuring cylinder.

The foam volume of $C_8$–$C_{18}$-alkylbenzyldimethylammonium chloride was determined as a comparison.

Result:

TABLE 3

Determination of the foaming behavior

| Active substance | Foam volume | |
|---|---|---|
| [g/l] | Example 13 | Comparison |
| 0.02 | 40 | 50 |
| 0.05 | 60 | 120 |
| 0.1 | 80 | 220 |
| 0.2 | 160 | 360 |
| 0.5 | 470 | 540 |
| 0.6 | 540 | 560 |

Determination of the preserving action:

a) Preservation of leather:

Chrome-tanned leather (wet blue) 1.8 mm thick is treated, after chrome tanning and in the same bath, with a microbicidal agent of the following active substance concentration over a period of one hour at a temperature of 35° C. at 30% by weight of liquor based on the pelt weight.

After the treatment, the leather is removed and stacked.

Table 4 indicates after which period (days, d) the treated leather was infected by molds at a storage temperature of 20° C.

Active substance:

Poly(didecylpolyoxyethylammonium borate)

TABLE 4

| Active substance concentration based on pelt weight [% by weight] | Infection with molds at 20° C. [d] |
|---|---|
| 0 | 9 |
| 0.1 | 150 |
| 0.2 | 200 |
| 0.5 | >200 |
| 1 | >200 |
| 2 | >200 |

The treated leather is infected with molds after a storage time not less than six months.

b) Preservation of hide:

Presoaked hide (cattle) from which the flesh had been removed is treated during the main soaking period in the barrel with a microbicidal agent of the following active substance concentration over a period of one hour at a temperature of 25° C. at 30% by weight of liquor based on the weight of the hide. After the treatment, the hide is removed and stacked.

Table 5 indicates after which period (day, d) the treated hide was infected by putrefactive bacteria at a storage temperature of 20° C.

Active substance:

8

Poly(didecylpolyoxyethylammonium borate)

TABLE 5

| Active substance concentration based on the weight of hide [% by weight] | Multiplication of putrefactive bacteria at 20° C. [d] |
|---|---|
| 0 | 2 |
| 0.4 | 14 |
| 1 | 20 |
| 2 | 30 |
| 5 | 45 |

The treated hide is infected with putrefactive bacteria after a storage time of not less than two weeks.

Determination of the virucidal properties

To test for the virucidal properties, a series of viruses which are pathogenic to humans are preincubated for 5 minutes with the active substance in question or only with medium. A representative of naked and a representative of coated viruses are selected from amongst the DNA viruses:

| | naked | coated |
|---|---|---|
| DNA virus | adenovirus type 5 | herpes simplex virus type 1 |
| | (adenoid 55) | cornea |

Suitable cell cultures are subsequently infected with these pretreated viruses. The medium-treated virus batches act as a control and are termed hereinafter as "untreated" virus batches. By comparing treated and untreated batches, the extent of the virucidal action of the disinfectant active substance is determined.

Methods:

Virus pretreatment with disinfectant:

250 µl of virus suspension (without fetal calf serum FCS) are incubated for 5 minutes at room temperature in the presence of 750 µl test solution. The test solutions contain, as active substances, coconut alkyldimethylbenzylammoniumchloride (CMBA), N-coconut alkylpropylenediamine-N, N-diguanidiniumdiacetate (CPGA), poly(didecylpolyoxyethylammonium borate (DPAB) and didecylmethylpolyoxyethylammonium propionate (DMOA) (in each case 500 µg/ml end concentration), Formalin (0.7% end concentration), and Dulbecco's Minimal Essential Medium (MEM). The virus suspensions are used at the highest concentration available (adeno $5 \times 10^4 \times CCID_{50}$, HSV-1 $5 \times 10^5 \times CCID_{50}$ (=$5 \times 10^7$ plaque-forming units); $CCID_{50}$ (cell culture infectious dose 50%) is the virus concentration at which 50% of the cells are damaged after incubation for 3 days at 37° C.

3.7 ml of MEM (without FCS) are added, and the batches are then centrifuged for 30 minutes at 4° C., 211,000×g (Beckman L7-55, SW 50.1) to remove the disinfectant from the batch. The virus-containing sediment is resuspended in 4.7 ml of MEM and recentrifuged for 1 hour under identical conditions. After resuspending the sediment in 1 ml of MEM, the virus batches which have undergone different pretreatments are tested in the cell culture assay for infectivity.

Cell culture assay:

Human cervix carcinoma cells (HeLa) are grown in Dulbecco's Minimal Essential Medium (MEM) in the presence of 10% fetal calf serum (FCS), and monkey kidney cells (Vero) are grown in Medium 199 in the presence of 5% FCS.

When the cell layer has reached confluence, the cells are harvested. The cell titer is adjusted with MEM (100 U/ml penicillin, 100 mg/ml streptomycin, 4% FCS) to 2.5×10³ cells/ml. 200 µl of this cell suspension are pipetted into 96-well microtiter plates (5×10² cells per well). The plates are subsequently incubated for 5 hours at 37° C. and 5% $CO_2$.

Serial dilutions were carried out with the pretreated and untreated virus suspensions in steps of 3 dilutions. HeLa cells are infected with a dilution (100 µl aliquots in MEM without FCS) of adenovirus 5 (adenoid 55). Vero cells are infected accordingly using herpes simplex virus type 1 (strain corneae). The incubation is subsequently continued for 3 days at 37° C.

All assays are carried out twice. After incubation for 72 hours at 37° C., when a complete cytopathogenic effect (CPE) is observed in the infection controls, the plates are assessed and subsequently stained with Neutral Red by the method of Finter.

Results:

TABLE 6

Effect of the disinfectant active substance on the virus concentration, indicated in multiples of the $CCID_{50}$.

| Virus type | Incubation time [min] | MEM (control) | CMBA (500) | CPGA (500) | DPAB (500) | DMOA (500) | Formalin (0.7%) (comparison) |
|---|---|---|---|---|---|---|---|
| Adeno | 5 | 19.683 | <3 |  |  |  | 1 |
|  |  | 2.187 |  | <9 |  |  | 1 |
|  |  | 2.187 |  |  | <9 |  | <1 |
| HSV-1 | 5 | 19.683 | <3 |  |  |  | <1 |
|  |  | 6.561 |  | <3 |  |  | <1 |
|  |  | 19.683 |  |  |  | <3 | <1 |

TABLE 7

Effect of the disinfectant active substances on the reduction of the virus titer

| Virus type | Incubation time [minutes] | Factor by which the virus concentration is reduced | | | |
|---|---|---|---|---|---|
| | | CMBA (500 µg/ml) | CPGA (500 µg/ml) | DPAB (500 µg/ml) | Formalin (0.7%) (comparison) |
| Adeno | 5 | >6561 |  |  | 6561 |
|  |  |  | >243 |  | 729 |
|  |  |  |  | >243 | >2187 |
| HSV-1 | 5 | >6561 |  |  | >19683 |
|  |  |  | >2187 |  | >6561 |
|  |  |  |  | >6561 | >19683 |

Discussion:

The reduction factor is determined to obtain a measure for the virucidal action of the active substances. First, the number of dilution steps required for infecting just 50% of the cell culture is determined in pretreated and untreated virus (Table 6). Untreated, active virus frequently requires a higher number of dilution steps, while a substantially smaller number of dilution steps should be required for the virucidal action of the test substance on pretreated virus since the infectiveness of the virus is only limited, or the virus is no longer infectious. The quotient formed from the dilution steps determined in the case of untreated and pretreated virus is given as the reduction factor (Table 7).

In the test model, the active substances employed have a marked virucidal action against representatives of naked and coated DNA viruses.

We claim:

1. A method of preserving and disinfecting animal hide with a low-foaming microbicidal agent comprising the steps of:

simultaneously reacting amines of the formulae I or II or mixtures thereof

-continued

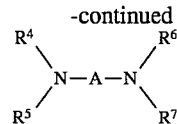

in which $R^1$ is $C_8$–$C_{22}$ alkyl, $C_8$–$C_{22}$ alkenyl $C_1$–$C_4$-alkyl, $R^2$ is hydrogen, $C_1$–$C_{22}$-alkyl, —$(C_2H_4O)_xH$, —$(C_3H_6O)_xH$, or —$CH_2CH_2CH_2NH_2$, $R^3$ is hydrogen, —$(C_2H_4O)_xH$, —$(C_3H_6O_xH$, or —$CH_2CH_2CH_{NH2}$, $R^4$ and $R^6$ are $C_1$–$C_4$-alkyl, —$(C_2H_4O)_xH$ or —$(C_3H_6O)_xH$, $R^5$ and $R^7$ are $(C_2HO)_xH$ or —$(C_3H_6O)_xH$, A is —$(CH_2)_n$—, —$(CH_2CH_2OCH_2CH_2)_n$— or —$(CH_2CH_2NHCH_2CH_2)_n$—, and x represents numbers from 1 to 55 and n is an integer from 1 to 20, with boric acid or its esters or salts while concurrently introducing alkylene oxide to form a crude solution of quaternary ammonium borate, mixing said crude solution with a solvent to form a stable solution or emulsion with a microbicidally effective amount of the quaternary ammonium borate, and introducing said animal hide into said stable solution or emulsion.

2. A method according to claim 1, wherein the stable solution or emulsion additionally contains microbicidal active substances selected from the group consisting of quaternary ammonium salts, amines, lower alcohols, aldehydes, and phenols.

3. A method according to claim 1, wherein the crude solution is mixed with an organic solvent selected from the group consisting of glycols, ethers, lower alcohols, or mixtures of glycols, ethers, and lower alcohols with chloroform or methylene chloride.

4. A method according to claim 1, wherein the crude solution is mixed with water.

5. A method according to claim 1, wherein the quaternary ammonium borate is present in 0.4 to 10.0% by weight based upon the weight of the animal hide.

6. A method according to claim 1, wherein the animal hide is selected from the group consisting of leather or cattle hide.

* * * * *